United States Patent [19]

Schwartz

[11] Patent Number: 5,496,810
[45] Date of Patent: Mar. 5, 1996

[54] PYRIMIDINE DEOXYRIBONUCLEOSIDE POTENTIATION OF COMBINATION THERAPY BASED ON 5-FLUOROURACIL AND INTERFERON

[75] Inventor: Edward L. Schwartz, White Plains, N.Y.

[73] Assignee: Montefiore Medical Center, Bronx, N.Y.

[21] Appl. No.: 226,499

[22] Filed: Apr. 12, 1994

[51] Int. Cl.$^6$ .................. A61K 31/505; A61K 31/70; A61K 38/21

[52] U.S. Cl. .................. 514/50; 514/12; 514/269; 514/889; 514/922; 424/85.4; 424/85.7

[58] Field of Search .................. 514/49, 50, 303, 514/269

[56] References Cited

U.S. PATENT DOCUMENTS

| | | | |
|---|---|---|---|
| 3,954,759 | 5/1976 | Anderson et al. | 514/303 |
| 4,895,727 | 1/1990 | Allen | 514/169 |

OTHER PUBLICATIONS

Biochemical Pharmacology, vol. 31, No. 22, pp. 3673–3682, 1982, Great Britain, Jan Balzarini et al.

Journal of Medicinal Chemistry, 1978, vol. 21, No. 2, pp. 228–231, Paul F. Torrence et al.

Antimicrobial Agents and Chemotherapy, 1978, vol. 1 13, No. 2, pp. 545–547, E. De Clercq et al.

Pharmacology, Chemotherapy 18:269–273, 1973, pp. 269–273, K. K. Gauri et al.

*Primary Examiner*—Douglas W. Robinson
*Assistant Examiner*—James O. Wilson
*Attorney, Agent, or Firm*—Hedman, Gibson & Costigan

[57] ABSTRACT

The applicants have discovered a method of treating malignancies which comprises administering effective amounts of 5-fluorouracil, interferon-α and a compound formula (I):

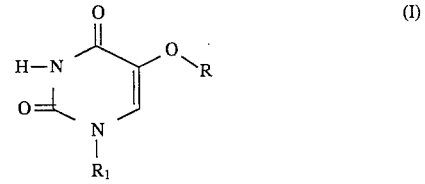

wherein R is selected is selected from the group consisting of alkyl of 1 to 5 carbon atoms, alkene of 2 to 5 carbon atoms and alkynyl of 2 to 5 carbon atoms; $R_1$ is 2'-deoxyribofuranosyl.

10 Claims, No Drawings

PYRIMIDINE DEOXYRIBONUCLEOSIDE POTENTIATION OF COMBINATION THERAPY BASED ON 5-FLUOROURACIL AND INTERFERON

BACKGROUND OF THE INVENTION

Field of the Invention

This invention relates to a novel combination of chemotherapeutic agents which are useful in the treatment of neoplastic diseases.

The combination is based on the addition of a pyrimidine deoxyribonucleoside compound to a combination of 5-fluorouracil and an interferon to provide an improved chemotherapeutic regimen for the treatment of neoplastic diseases or the treatment of malignant neoplasms.

In the prior art combinations of 5-fluorouracil and interferon-α have been described for the treatment of malignant neoplasms as well as combinations of 5-fluorouracil and deoxynucleosides such as 2'-deoxyinosine.

The present invention is concerned with a novel treatment regimen which combines 5-fluorouracil, interferon-α and a deoxynucleoside.

It is therefore an object of the invention to provide a novel therapeutic regimen which is based on the combined administration of a pyrimidine deoxyribonucleoside, 5-fluorouracil and interferon-α.

It is also an object of this invention to provide a novel method for the treatment of neoplastic diseases which uses a particular dose of a pyrimidine deoxyribonucleoside, 5-fluorouracil and interferon-α.

These and other objects of the invention will become apparent from a review of the specification.

SUMMARY OF THE INVENTION

The present invention is directed to a novel anti-neoplastic treatment regimen which comprises 5-fluorouracil and a compound of the formula:

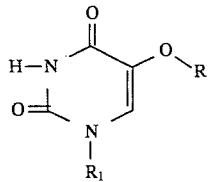

wherein R is selected is a straight or branched chain group selected from the group consisting of alkyl of 1 to 5 carbon atoms, alkene of 2 to 5 carbon atoms, alkynyl of 2 to 5 carbon atoms; $R_1$ is 2'-deoxyribofuranosyl. Interferon-α is preferred but other interferons such as beta and gamma interferon may be employed.

DETAILED DESCRIPTION OF THE INVENTION

Interferon-α potentiates the cytotoxicity of 5-fluorouracil in vitro and the in vivo efficacy of this combination has been demonstrated in the treatment of advanced colorectal cancer. The present invention is based on the discovery that compounds of the formula:

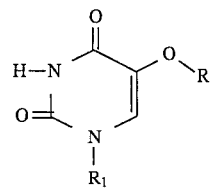

wherein R is selected is selected from the group consisting of alkyl of 1 to 5 carbon atoms, alkene of 2 to 5 carbon atoms and alkynyl of 2 to 5 carbon atoms; $R_1$ is 2'-deoxyribofuranosyl will potentiate the effectiveness of the combination of interferon-α and 5-fluorouracil. Preferred compounds of Formula I include 5-ethoxy-2'-deoxyuridine and 5-(2-propynyloxy)-2'deoxyuridine.

The three component therapeutic regimen of the invention is based on the use of the following dosages of the three drugs:

(a) 5-fluorouracil is administered at a dose of 600 to 1000 $mg/m^2$ given daily for 4 to 10 days parenterally, preferably intravenously in divided doses or continuously followed by 4 to 10 days of rest.

(b) interferon-α is administered at a dose of 2 to 40 and preferably 5 to 9 million international units 3 to 7 times per week subcutaneously.

(c) deoxyribonucleoside 5 to 50mg/kg of body weight per day, and preferably 3 to 20 mg/kg of body weight per day, given continuously or in 4 to 6 divided doses concomittantly with the 5-fluorouracilo A preferred dosage regimen is about 750 $mg/M^2/day$ of 5-fluorouracil for about 5 days followed by a one week rest period along with 2–40 million international units of recombinant interferon-α/day subcutaneously, 3 to 7 times per week. A preferred dose for the interferon-α is 9 million international units three times per week and a preferred dose of the deoxyribonucleoside is about 10 mg/kg of body weight per day. The course of therapy may be carried out for a period of 2–52 weeks. Depending on the therapeutic response and the manifestation of unacceptable side effects, the dose may be increased or decreased within the general description set forth herein.

The drugs are preferably administered parenterally as a solution of the drug in normal saline.

The invention may be used to treat malignancies which are sensitive to the described treatment regimen. These malignancies include colorectal carcinoma, espohageal carcinoma, stomach carcinoma, pancreatic carcinoma, liver carcinoma, small bowel carcinoma, biliary carcinoma, breast carcinoma and adenocarcinoma of unknown origin.

The effectiveness of the combination of the present invention have been demonstrated against the HT29 human colon carcinoma cell line.

The compound 5-(2-propynyloxy)-2'-deoxyuridine was prepared according to the methods of Torrence et al., J. Med. Chem. 21:228–231, 1978 and Otter et al., J.Org. Chem. 37:2858–2863, 1972.

The compound 5-ethoxy-2'-deoxyuridine was prepared as follows: The precursor compound 5-hydroxy-2'-deoxyuridine was prepared by modifying the procedure described in the literature (E. G. Podrebarac and C. C. Cheng, Synthetic Procedures in Nucleic Acid Chemistry, Vol. 1, p412–413, W. W. Zorbach and R. S. Tipson Eds., Interscience Publishers, NY 1968) as follows: bromine (1.1ml, 1 equivalent) is added dropwise at room temperature to a stirred solution of 5g. of 2'-deoxyuridine (Sigma) in 100ml of water until a pale color persisted. The color was then discharged by the addition of a small crystal of sodium thiosulfate. Pyridine (25ml) was added in one portion and the mixture was held at room temperature for 17 hours. Solvents were then removed by evaporation in vacuo and ethanol (3 ×50ml) was added to and evaporated from the syrupy residue. A solution of the final residue in 50ml of ethanol deposited colorless crystals of 2'-deoxy-5-hydroxyuridine when held for 5 hours at 5° C. The yield of the first crop was 2.3g.

The 2'-deoxy-5-hydroxyuridine (244 mg.,1mmol) was suspended in a mixture of methanol (10ml) and water (5ml) at room temperature, and 1 ml of 1.0N sodium hydroxide solution (1mmol) was added to generate the monoanion. Ethyl bromide (0.312ml, 4mmol) was added, and the reaction mixture was stirred for 16 hours. The solvent was removed in vacuo, and ethanol was added to and evaporated from the residue. The desired 5-ethoxy product was separated from small amounts of the 3 ethyl-5-ethoxy dialkyl byproduct by chromatography on a silica gel column using chloroform-methanol (9:1, v/v) as the solvent. Following crystallization from absolute ethanol, 5-ethoxy-2'-deoxyuridine was obtained in 52% yield (140 mg); mp 179°–181° C.; $^1$H NMR (methyl sulfoxide-$d_6$),δ11.38 (1H, br s, NH), 7.58 (1H, s, H-6), 6.18 (1H, t, H-1'), 5.19 (1H, d, 3'-OH), 5.09 (1H, t, 5'-OH), 4.25 (1H, m, H-3'), 3.79 (3H, m. H4'and OCH$_2$CH$_3$ ), 3.59 (2H, br s,H-5'and H-5"), 2.10 (2H, m, H-2'and H-2") and 1.23ppm (3H, t, OCH$_2$CH$_3$). Anal. Calcd. for $C_{11}H_{16}N_2O_6$ C, 48.53; H, 5.92; N, 10.29. Found: C, 48.69; H, 6.0-1; N, 10.36.

EXAMPLE

This example demonstrates the antineoplastic activity of 5-ethoxy-2'-deoxyuridine or 5-propynyl-2'deoxyuridine in combination with 5-fluorouracil or in combination with 5-fluorouracil and interferon-α.

HT-29 human carcinoma cells (ATCC No. HTB-38) were maintained in RPMI 1640 with 10%v/v fetal bovine serum (GIBCO) in a humidified, 5% CO$_2$ atmosphere at 37° C. Cells were plated in 24 well plates (150 cells per well) in RPMI 1640 medium with 10% v/v dialyzed fetal bovine serum. After allowing cell attachment to proceed overnight, combinations of interferon-α (500units/ml; Roferon-A, Roche Labs.), 5-ethoxy-2'-deoxyuridine (150μM) or 5-propynyl-2'-deoxyuridine (150μM) in the presence of increasing concentrations of 5-fluorouracil (as specified in the Table) were added. The various agents were diluted in phosphate-buffered saline (PBS), and control wells received vehicle alone. After 72 hours, drug containing medium was removed and replaced with RPMI 1640 with 10%v/v fetal bovine serum. Cell colonies were allowed to grow for an additional 7–10 days, at which point they were stained and counted. Control cloning efficiency in the absence of drug averaged 60%; all data are expressed relative to the control cloning efficiency. Data are means of at least 3 determinations. The IC$_{50}$ values for 5-fluorouracil were calculated graphically by determining the concentration of 5-fluorouracil that reduced cloning efficiency by 50% from the cloning efficiency value measured in the absence of 5-fluorouracil. The results were as follows:

| | Cloning Efficiency (% of control) | | | | | |
|---|---|---|---|---|---|---|
| 5-FU | CONT | IFN | 5-ETH | 5-PRO | 5-ETH + IFN | 5-PRO + IFN |
| 0 | 100% | 95% | 89% | 105% | 97% | 75% |
| 0.025 μM | — | — | — | — | 89% | 76% |
| 0.05 μM | — | — | 81% | 100% | 81% | 49% |
| 0.10 μM | — | — | 80% | 81% | 38% | 29% |
| 0.15 μM | — | — | — | — | 9% | 7% |
| 0.25 μM | 104% | 97% | 60% | 51% | 0% | 2% |
| 0.50 μM | 93% | 83% | 38% | 26% | — | — |
| 1.0 μM | 87% | 56% | 13% | 9% | — | — |
| 1.5 μM | 60% | 18% | 4% | 4% | — | — |
| 2.0 μM | 55% | 8% | — | 2% | — | — |
| 3.0 μM | 27% | 1% | — | 0% | — | — |
| 4.0 μM | 5% | — | — | — | — | — |
| IC$_{50}$ | 2.0 μM | 1.1 μM | 0.35 μM | 0.26 μM | 0.08 μM | 0.08 μM |

5-FU = 5-fluorouracil
Cont = control, PBS (vehicle)
IFN = interferon-α (Roferon-A, Roche Labs) 500 u/ml
5-ETH = 5-ethoxy-2'-deoxyuridine (150 μM)
5-PRO = 5-propynyloxy-2'-deoxyuridine (150 μM)

The following Table provides data which shows the increased effect of the particular chemotherapeutic agents at the stated concentrations of 5-fluorouracil:

| Additions | 5-FU IC$_{50}$ | Change |
|---|---|---|
| None | 2.0 μM | — |
| Interferon-α (500 u/ml) | 1.1 μM | 1.8* |
| 5-ethoxy-2'-deoxyuridine (150 μM) | 0.35 μM | 5.7* |
| 5-ethoxy-2'-deoxyuridine (150 μM) and interferon-α (500 u/ml) | 0.08 μM | 25.0* |
| 5-propynyloxy-2'-deoxyuridine (150 μM) | 0.26 μM | 7.7* |
| 5-propynyloxy-2'-deoxyuridine (150 μM) interferon-α (500 u/ml) | 0.08 μM | 25.0* |

*Indicates a value significantly different from control, p < 0.01. IC$_{50}$ values were calculated from cloning efficiency data obtained after 3 days of drug treatment. Data are means from at least 4 experiments. The interferon-α that was employed was Roferon-A.

The test data establishes that the compound 5-ethoxy-2'-deoxyuridine increases the potency (i.e. reduces the IC$_{50}$) of the cancer chemotherapeutic drug 5-fluorouracil by a factor of 5.7 when used alone and when used in combination with interferon-α, the potency is increased by a factor of 25.0.

The effect of interferon and the tested nucleosides on the activity of 5-fluorouracil is clearly demonstrated in the above identified tests. Under the conditions of the test, (72 hours of 5-fluorouracil treatment followed by growth in the absence of drug for 10 days) a 50% reduction in colonies is seen when 2 μM of 5-fluorouracil is employed. Interferon-α used concurrently with the 5-fluorouracil lowered the $IC_{50}$ for 5-fluorouracil to 1.1μM. Both 5-propynyloxy-2'-deoxyuridine and 5-ethoxy-2'-deoxyuridine increased the cytotoxicity of 5-fluorouracil by 7.7 and 5.7 times, respectively and when interferon is added to the combination, the cytotoxicity is increased by 25.0 times.

The data establishes that the combined use of the substituted deoxyuridines and 5-fluorouracil provides a substantial increase in the cytotoxicity of 5-fluorouracil. This potentiation of activity allows the clinicjan to achieve a therapeutic effect which is much greater than the effect of 5-fluorouracil, alone, which is obtained at currently employed doses. This will permit the use of a lower dose of 5-fluorouracil without a corresponding reduction in the therapeutic effect.

We claim:

1. A method of treating a neoplasm which is sensitive to the combination of 5-fluorouracil, interferon-α and a compound of formula (I):

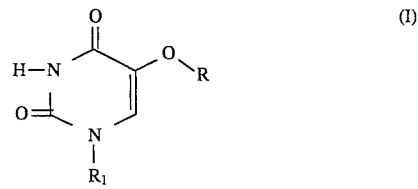

wherein R is selected from the group consisting of alkyl of 1 to 5 carbon atoms, alkene of 2 to 5 carbon atoms and alkynyl of 2 to 5 carbon atoms; $R_1$ is 2'-deoxyribofuranosyl, said method comprising administering to a host an amount of said combination which is effective to treat a neoplasm which is sensitive to the combination.

2. A method as defined in claim 1 wherein the compound of Formula I is 5-(2-propynyloxy)-2'-deoxyuridine.

3. A method as defined in claim 1 wherein the compound of Formula I is 5-ethoxy-2'-deoxyuridine.

4. A method as defined in claim 2 wherein the interferon is interferon-α.

5. A method as defined in claim 3 wherein the interferon is interferon-α.

6. A method as defined in claim 1 wherein 5-fluorouracil is administered to a host at a dose of 600 to 1000 mg/m² given daily for 4 to 10 days parenterally followed by 4 to 10 days of rest; interferon-α is administered at a dose of 2 to 40 international units 3 to 7 times per week; and 5 to 50 mg/kg of body weight deoxyribonucleoside in 4 to 6 divided doses.

7. A method as defined in claim 6 wherein the deoxyribonucleoside is 5-(2-propynyloxy)-2'-deoxyuridine.

8. A method as defined in claim 1 wherein the deoxyribonucleoside is 5-ethoxy-2'-deoxyuridine and the neoplasm is colorectal carcinoma.

9. A method as defined in claim 6 where the interferon is interferon-α-2-a.

10. A method as defined in claim 1 where the neoplasm is colorectal carcinoma.

* * * * *